United States Patent [19]

Wendorff

[11] 4,128,100
[45] Dec. 5, 1978

[54] SUTURE

[76] Inventor: Erwin R. Wendorff, 1303 Garden La., Reading, Pa. 19611

[21] Appl. No.: 730,798

[22] Filed: Oct. 8, 1976

[51] Int. Cl.² .................... A61L 17/00; A61B 17/04
[52] U.S. Cl. .............................. 128/335.5; 128/337
[58] Field of Search .............. 128/334, 335, 335.5, 128/337, 327; 29/517; 140/93.4, 106

[56] References Cited

U.S. PATENT DOCUMENTS

| | | | |
|---|---|---|---|
| 1,277,305 | 8/1918 | Gerrard | 140/93.4 |
| 2,093,145 | 9/1937 | Carruthers | 128/335.5 |
| 2,583,625 | 1/1952 | Bergan | 29/517 |
| 2,881,762 | 4/1959 | Lowrie | 128/337 |
| 3,545,008 | 12/1970 | Bader | 128/334 R |
| 3,802,438 | 4/1974 | Wolvek | 128/335 |
| 4,037,603 | 7/1977 | Wendorff | 128/335.5 |

FOREIGN PATENT DOCUMENTS 494960  6/1919  France ...................... 128/335

*Primary Examiner*—Dalton L. Truluck
*Attorney, Agent, or Firm*—Miller & Prestia

[57] ABSTRACT

A surgical system for use in forming a looped support of body portions of mammals consisting of a suture comprising a thin, narrow, flexible strip; a cylindrical sleeve through which the ends of said suture are placed, and means for crimping or attaching said sleeve so as to interlock the ends of said suture when said end portions are in lapping relationship.

5 Claims, 5 Drawing Figures

SUTURE

BACKGROUND OF THE INVENTION

1. Field of the Invention

The invention relates to a system for the treatment of stress urinary incontinence and for the treatment of the incompetent cervix during pregnancy. More particularly, the present invention is particularly adaptable for employment in operations such as that entitled "Urethrovaginal Fixation to Cooper's Ligament for Correction of Recurrent Stress Incontinence". However, it is understood that the use of the present system can be utilized in other operations whereby support or clamping of the body portions have been previously performed by means of sutures or clamps.

2. Description of the Prior Art

Heretofore, in operations such as referred to above and as described in an article entitled "Urethrovaginal Fixation to Cooper's Ligament (Burch) in the Treatment of Incontinence" by Erfurth Nielsen and Finn Lundvall of Copenhagen, Denmark, the article having been published in Acta Scand. Suppl. 433: 118-120, 1973, which discloses the use of catgut sutures which are applied on each side of Cooper's Ligament that are passed through the perivaginal fascia on each side of the urethra after dissection of the space of Retzius and adequate exposure of the bladder and urethra. Each suture is then passed through the most easily reached point of Cooper's ligament and tied. However, this procedure has presented serious problems as, for example, the procedure is very time consuming for the surgeon and the patient is exposed for an excessive period to trauma. Also, the sutures do not necessarily uniformly distribute the stress as in many instances, some will be tighter than others. In addition, it has been found that in a number of instances, the sutures break if the patient should have a coughing spell or be subjected to other spasms.

U.S. Pat. Application Ser. No. 576,960 filed May 13, 1975, now U.S. Pat. 4,037,603, of applicant has improved on the system disclosed by Nielsen et al by providing a suture comprising a highly flexible, elongated strip of surgical steel having means for interlocking each end of the suture to selected portions along the strip in treating incontinence in female patients. Moreover, the sutures require greater precision in their manufacture and more dexterity by the surgeon to insert in place.

For the treatment of the incompetent cervix during pregnancy an operation as described in an article entitled "A New Method of Operative Treatment of Habitual Abortions in the Second Trimester of Pregnancy" by V.N. Shirodkar has been published in Antiseptic 52:299, 1955. However, the procedure described by Shirodkar requires the stitching of sutures so as to be time consuming and may cause scarring.

SUMMARY OF THE INVENTION

The principal object of the present invention is the provision of a system which eliminates the problems heretofore encountered in operations for the treatment of stress urinary incontinence and for the treatment of the incompetent cervix during pregnancy.

Another object of the present invention is the provision of a suture and locking means for use in operations referred to in the foregoing object, and which is also adapted for use in other operations, in which the suture may be individually formed in a loop with its end portions in interlocking engagement.

Another object of the present invention is the provision of a suture attaining the foregoing objects which is simple in design, safe and economical to manufacture.

A further object of the present invention is the provision of a suture which may be employed as a single suture without the requirement of stitching as previously required in certain operations.

The foregoing and other objects of the invention, as will become more apparent, are attained utilizing the system of the present invention and the method of its employment, the system comprising a flexible suture, a sleeve for interlocking the ends of the suture so as to form a loop, and a means for crimping or attaching the sleeve so as to permanently fasten the ends together.

In the employment of the present system for the treatment of stress urinary incontinence, the surgeon applies the suture so as to maintain a high posterior urethra vesical angle, as described by Mattingly in "Surgical Techniques for the Treatment of Stress Urinary Incontinence," Kelly Urethral Plication, Ethicon.

In a treatment of the incompetent cervix the surgeon places the suture submuscosally at the level of the internal os and then crimps or attaches a sleeve over the ends of the suture once the proper tension has been established.

DESCRIPTION OF THE PREFERRED EMBODIMENTS

Figure 1:
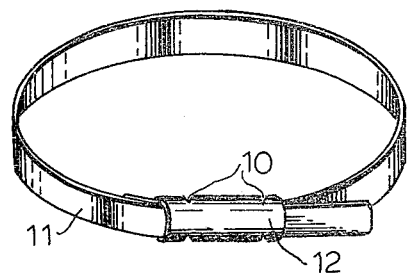
FIG. 1 is a perspective view of a suture and sleeve formed in a loop in accordance with the instant invention.

Referring now to the drawings and particularly to FIG. 1, there is shown a flexible surgical suture which is held in a looped position by a cylindrical sleeve 12 having at least one crimped portion 10.

Figure 1A:
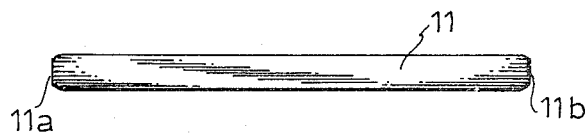
FIG. 1a is a view of the suture of FIG. 1.

As seen in FIG. 1a, the suture 11 has an elongated body portion with rounded ends 11a and 11b. The suture may be made of any physiologically acceptable material which is flexible and capable of withstanding stress. The suture 11 may be made of any flexible and pliable material including silk, polyester fibers, including Tevdek II (Registered trademark) a Teflon-impregnated Dacron filament that is marketed by DuPont Corporation, elastomer coated metallic sutures, and the like.

Figure 1B:
FIG. 1b is a perspective view of a sleeve for use in accordance with the present invention.

As noted in FIG. 1b, the sleeve consists of a ferrule-shaped configuration of a crimpable physiologically acceptable material, especially, surgical steel, such steel preferably being of the ASTM designation F138-71, 316LC stainless steel, titanium or titanium alloy of the designation F67-66 or F137-70.

Figure 2:
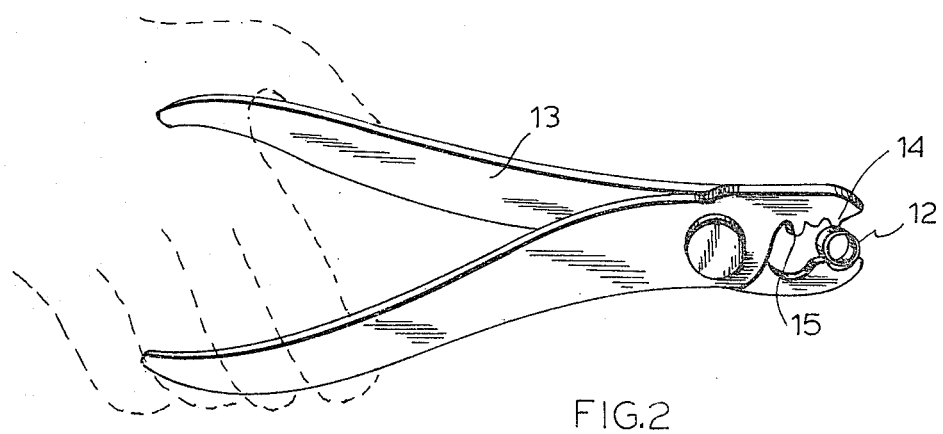
FIG. 2 is a perspective view of a crimping tool for crimping the sleeve onto the suture in accordance with the present invention.
Figure 3:
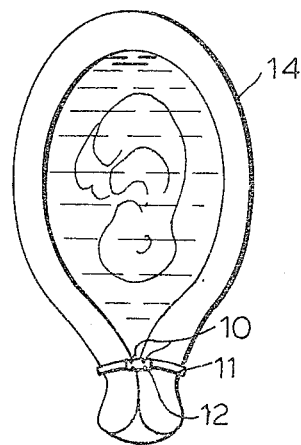
FIG. 3 illustrates the suture of FIG. 1 in the locked position in the treatment of the incompetent cervix during pregnancy.

FIG. 2 shows one form of crimping or attaching tool 13 which may be utilized in connection with the present invention for placing in sleeve 12 the crimps 10. Preferably, the crimping tool is provided with a plurality of crimping areas to accommodate the different sizes of sleeves which may be utilized in various operations. The use of portion 14, because of the small working area has been found to be effective for crimping the sleeve during the operation for the treatment of the incompetent cervix. Portion 15 has been effectively used in crimping the sleeve during the operation correcting stress urinary incontinence.

The employment of the system of the present invention has, for example, in the operation previously referred to, namely "Urethrovaginal Fixation to Cooper's Ligament in the Treatment of Incontinence" and the manner of forming the loop is as follows:

After the surgeon makes an incision extending laterally between the pelvic bones of the patient and the surgeon's performance of further preparatory steps, he inserts the suture through one side of Cooper's ligament and/or the conjoined tendon supporting the urethra and out the other side. Following insertion of the suture, the extending ends are placed within a sleeve, the suture is then suitably tightened around the body portion and crimped so as to form a permanent loop.

In the case of treatment of the incomplete cervix during pregnancy, after the preparatory steps by the surgeon, the suture 11, which is preferably a silicon-tendon graft is placed submuscosally at the level of the internal os 14, the ends are introduced through the sleeve and crimped or attached after proper tension is established.

The above described system fully obtains the objects of the invention previously set forth. Of particular importance is the very substantial reduction in the time required for the suturing operation and the consequent reduction in the period to which the patient is subjected to trauma. The crimping or attaching of the sleeve over the ends of the suture ensures maintenance of the suture in place which is a matter of major importance. Also, the system may be readily manufactured and at a nominal cost. Moreover, instructions on how to perform the crimping operation are surprisingly simple for the performing surgeon to follow.

It will be apparent that many modifications and variations can be effected without departing from the scope of the novel concepts of the present invention, and the illustrative details disclosed are not to be construed as imposing unnecessary limitations on the invention.

What is claimed is:

1. A method for the treatment of stress urinary incontinence or the incompetent cervix in pregnancy comprising forming a loop from a flexible surgical suture submucosally at the level of the internal os of a mammal, placing the ends of said suture in lapping relationship in a cylindrical crimpable sleevem and crimping said sleeve so as to impinge on the ends of said suture and lock the suture in the form of a loop.

2. The method of claim 1, wherein said sleeve is formed of surgical steel.

3. The method of claim 1, wherein said sleeve is formed of a titanium alloy.

4. The method of claim 1, wherein said suture is a silicon-tendon graft.

5. A method for the treatment of stress urinary incontinence or the incompetent cervix in pregnancy comprising forming a loop from a thin, narrow, flexible surgical suture submucosally at the level of the internal os of a mammal, placing the ends of said suture in lapping relationship in a cylindrical sleeve, and attaching said sleeve to the ends of said suture in the form of a loop.

* * * * *